United States Patent [19]

Reynolds

[11] 4,086,818

[45] May 2, 1978

[54] ULTRASONIC IMAGING APPARATUS

[75] Inventor: Charles A. Reynolds, West Haven, Conn.

[73] Assignee: SmithKline Instruments, Incorporated, Sunnyvale, Calif.

[21] Appl. No.: 771,450

[22] Filed: Feb. 24, 1977

[51] Int. Cl.² .......................................... G01N 29/04
[52] U.S. Cl. ..................................................... 73/620
[58] Field of Search .............. 73/67.7, 67.8 R, 67.8 S, 73/67.9; 128/2 V; 340/1 R, 5 MP; 358/112

[56] References Cited

U.S. PATENT DOCUMENTS 3,453,871  7/1969  Krautkramer ................... 73/67.8 R

OTHER PUBLICATIONS

G. Baum, Aids in Ultrasonic Diagnosis, J.A.S.A., Dec. 1970, vol. 48, No. 6, Pt. 2, pp. 1407–1412.
J. M. Reid, Evaluation of Intensity–Modulated Recording for Ultrasonic Diagnosis, J.A.S.A., Nov. 1968, vol. 44, No. 5, pp. 1319–1323.

Primary Examiner—Richard C. Queisser
Assistant Examiner—John P. Beauchamp
Attorney, Agent, or Firm—Ervin B. Steinberg; Philip J. Feig

[57] ABSTRACT

An ultrasonic imaging apparatus is disclosed having a display selectably interchangeable between a shades of gray image presentation and an edge enhanced image presentation to facilitate distance measurements of the image on the display screen. A first filter network processes echo responsive electrical signals for preserving echo amplitude information in a shades of gray image presentation and a second filter network processes the echo responsive electric signals for enhancing only the leading edge of the electrical signals.

2 Claims, 7 Drawing Figures

ULTRASONIC IMAGING APPARATUS

BRIEF SUMMARY OF THE INVENTION

The invention concerns an ultrasonic imaging apparatus and more specifically concerns an imaging apparatus selectively providing either a shades of gray display or an edge enhnaced display for facilitating critical distance measurements of the image on the display screen.

Ultrasonic imaging of workpieces, especially fetuses or human organs is well known in the art. The general procedure is to acoustically couple an ultrasonic transmit-receive transducer probe to the surface of an object or the skin of a subject and cause the probe to transmit an ultrasonic search signal into the object or body. Upon intercepting an acoustic discontinuity, a portion of the search signal is reflected back toward the probe as an echo signal. The probe converts the received echo signal into an electrical signal which is further processed and displayed on the screen of a cathode ray tube. In a conventional shades of gray display, the echo signals are displayed with varying degrees of brightness responsive to the amplitude of the echo signal for providing an image of the acoustic discontinuity, for instance, the head of a fetus. Since, in practice, the edge of an acoustic discontinuity is generally uneven or rough, the edge of the image is "blurred". The blurred image heretofore has created problems when it has been necessary to measure a distance of a portion of a display, such as the size of the fetal cranium. It has been found that when using a shades of gray display measurement errors are caused by the difficulty in determining the exact location of the edge of the image. Likewise, the blurred image creates difficulties in determining the distance from an acoustic discontinuity to another structure in the object under examination.

The present apparatus provides means for selectively switching from a shades of gray display to a so-called edge enhanced image in which the edge or outline of the image is enhanced or brightened. The provision of a bright, sharp image contour line eases the subsequent distance measurement performed on the display screen image.

The edge enhanced display is generated by selectively switching from a first filter circuit to a second filter circuit disposed in the video signal processing circuit. In a shades of gray display it is essential that the echo amplitude information provided from the probe, for instance, the peak values or more importantly the logarithmic values be preserved and displayed on the screen as point images of varying intensity. The echo responsive electrical signal is filtered to reduce noise and other spurious signals, but the amplitude information is retained. In contrast, when a distance measurement is to be made, noise and other spurious signals are reduced from the echo responsive electrical signals, but the filter smooths the amplitude information contained in the electrical signal. The filtered signal is then differentiated for providing a single point on the display screen, the point being representative of the edge of the acoustic discontinuity. By printing a series of such points on the screen, a sharp, high resolution image of the outline of an acoustic discontinuity is presented. The operator then need only measure the distance between the sharp image points to perform a distance measurement.

A principal object of the present invention is, therefore, the provision of selectively providing an edge enhanced ultrasonic imaging display apparatus.

Another object of the invention is the provision of an ultrasonic imaging apparatus having a display selectably interchangeable between a shades of gray image presentation and an edge enhanced image presentation.

Further objects of the invention will become more clearly apparent when the following description is read in conjunction with the accompanying drawings.

DETAILED DESCRIPTION OF THE INVENTION

Figure 1:
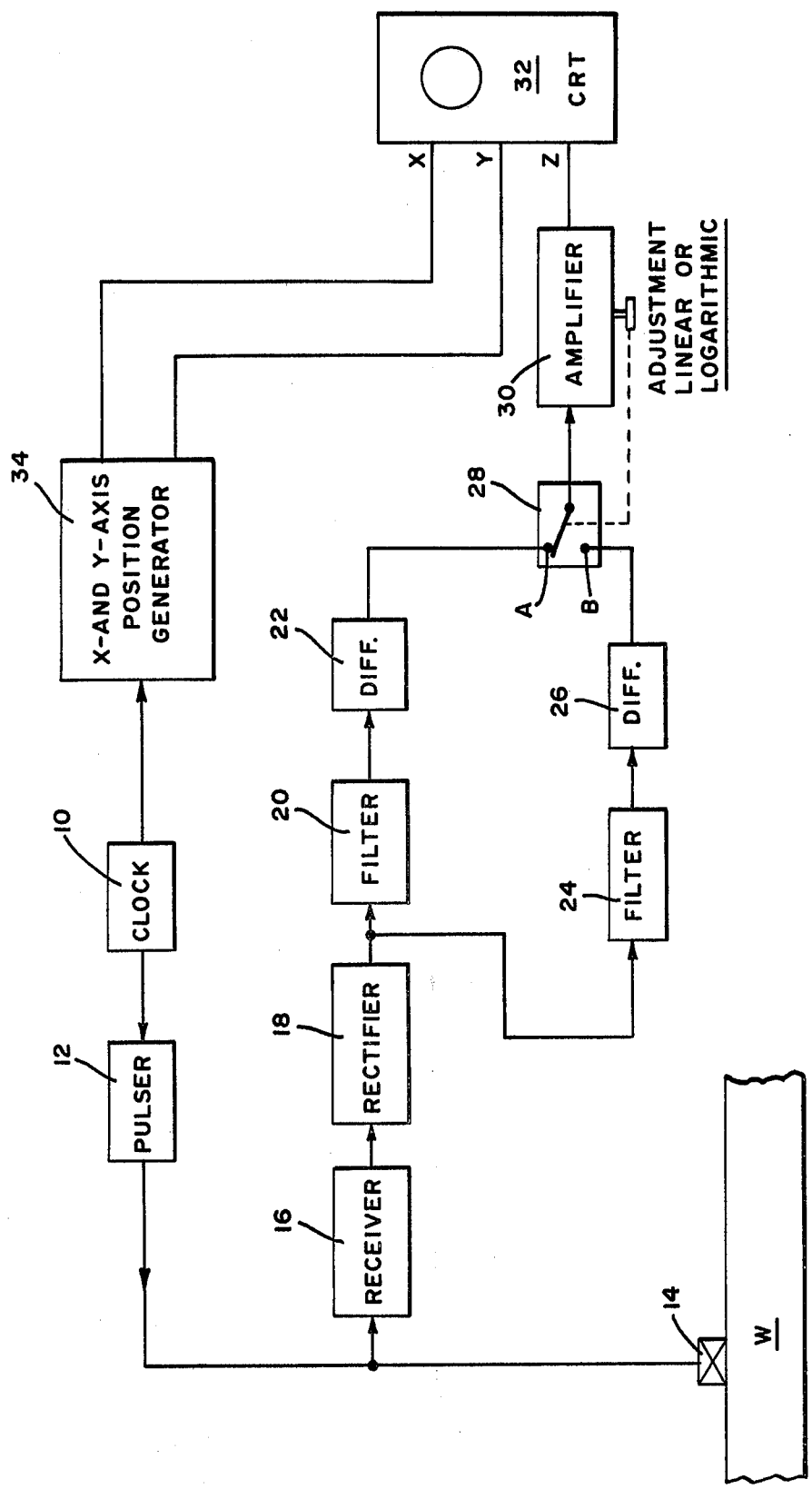
FIG. 1 is a schematic block circit diagram of a preferred embodiment of the invention.
Figure 2:
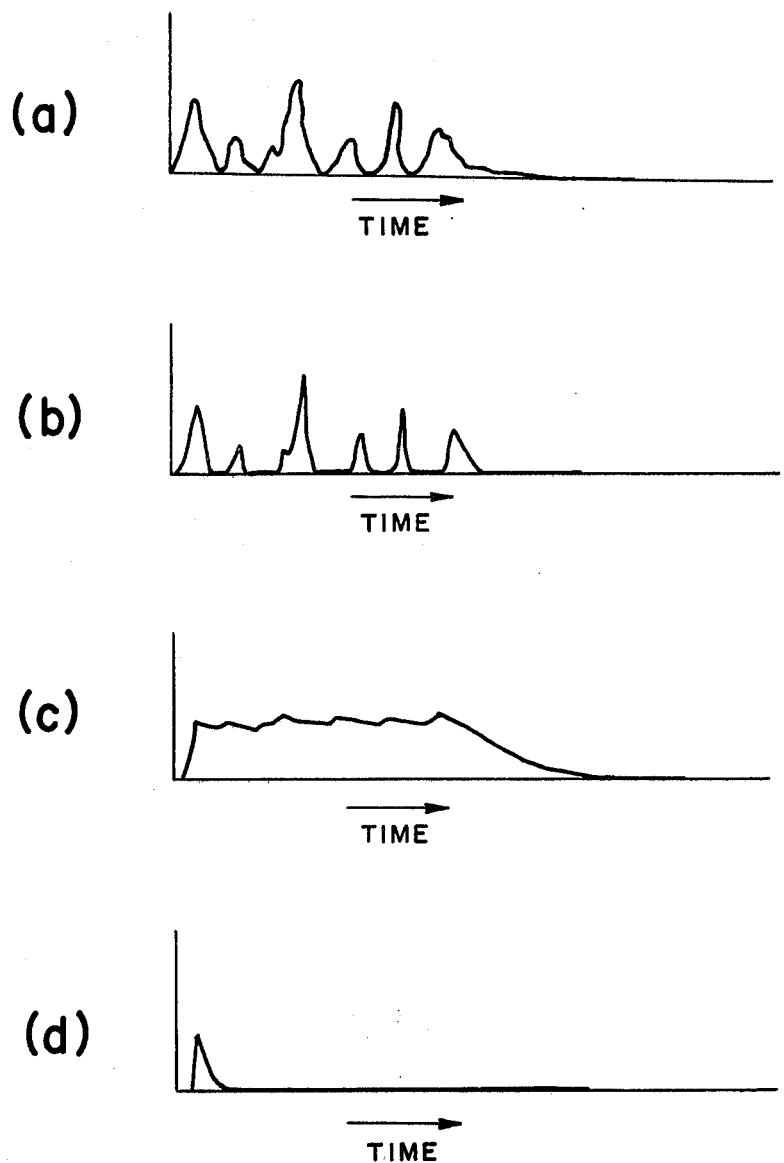
FIGS. 2a–2d are graphical representations of signal waveforms generated in the circuit per FIG. 1.

Referring now to the drawings and FIG. 1 in particular, there is shown a schematic electrical circuit block diagram of a preferred embodiment of the invention. A clock 10 provides timing pulses to a pulser 12 which, in turn, provides trigger pulses to an ultrasonic transmit-receive transducer probe 14 causing the probe 14 to periodically transmit an ultrasonic energy search signal into an object W. In a particular embodiment, the probe 14 may comprise an array of juxtaposed piezoelectric elements and the object W under examination may be a human body. Upon intercepting an acoustic discontinuity in the object W, a portion of the search signal is reflected back to the probe 14 as an echo signal. The reflected echo signal is converted by the probe 14 into an electrical signal and provided to receiver circuit 16. The echo responsive electrical signal at the output of receiver circuit 16 is provided to a full wave rectifier circuit 18. As shown in FIG. 2a, the signal corresponding to the search signal intercepting an acoustic discontinuity includes a series of varying amplitude signals containing noise and other spurious signals. The shape of the echo responsive signal waveform results from the uneven or irregularly shaped edge of the acoustic discontinuity. Moreover, an organ in the body is usually surrounded by tissue, ligaments and other structures each of which reflects a portion of the search signal.

The rectified signal at the output of the rectifier circuit 18 is fed to a filter network 20 and a differentiator circuit 22 and a second parallel connected filter network 24 and differentiator circuit 26. The two filter-differentiator circuits are connected to respective contacts of a switch 28. The switch 28 is selectively connected to either contact A or B for coupling either the signal from differentiator circuit 22 or the signal from differentiator circuit 26 to the input connection of amplifier 30.

The amplified video signals at the output connection of amplifier 30 are provided to the writing electrode (Z-axis input) of a cathode ray tube 32 or to the write input of a display device.

The amplifier 30, in a preferred embodiment, changes gain characteristics responsive to the condition of switch 28. When a shades of gray image presentation is desired, for instance, the amplifier 30 is designed for providing a linear gain characteristic for preserving signal amplitude information. Alternatively, when the switch 28 is in the position for providing an enhanced edge image presentation, the amplifier 30 is designed for providing a nonlinear, exponential gain characteristic for providing greater amplifier dynamic range.

620 kilohertz and thereafter the gain curve decreases at a rate of approximately 14 db/octave.

TABLE 1

| Component | Value | Component | Value |
| --- | --- | --- | --- |
| Resistor 100 | 1 kilohm | Inductor 112 | 220 microhenries |
| Resistor 102 | 3.3 kilohm | Inductor 114 | 220 microhenries |
| Resistor 104 | 3.3 kilohm | Capacitor 116 | 100 picofarads |
| Resistor 106 | 3.3 kilohm | Capacitor 118 | 200 picofarads |
| Resistor 108 | 1 kilohm | Capacitor 120 | 200 picofarads |
| Inductor 110 | 220 microhenries | Capacitor 122 | 100 picofarads |

When switch 28 is connected to the uppermost contact A, as shown, the rectified signal per FIG. 2a is conducted through filter network 20 and differentiator circuit 22 and appears at output of differentiator circuit 22 as shown in FIG. 2b. Noise, spurious signals and the like accompanying the signal have been reduced and the amplitude of each spike-shaped signal is commensurate with the amplitude of the corresponding signal shown in FIG. 2a. The signal per FIG. 2b is conducted through switch 28 and amplifier 30 to the writing electrode of a cathode ray tube for providing a shades of gray image presentation on the screen.

As is known in the art, additional circuitry including an X- and Y- axis position generator 34 is provided for synchronizing the position of the display to the depth from the surface at which the acoustic discontinuity is disposed and to the location of the acoustic discontinuity along the length of the probe array 14 or along the surface of the object W. Such circuitry does not form a part of the invention.

Figure 3:
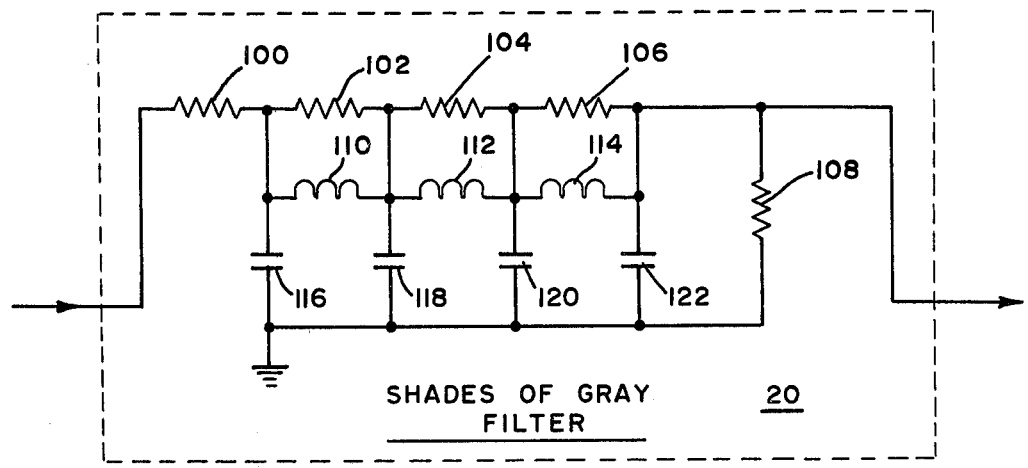
FIG. 3 is a schematic electrical circuit diagram of a preferred embodiment of a filter network for processing video signals to be used in a shades of gray display.

A preferred embodiment of the filter network 20 is shown in detail in FIG. 3. The input connection is coupled to the first end of resistor 100. The other end of resistor 100 is connected to one side of the parallel combination of resistor 102 and inductor 110 and to the first side of capacitor 116. The other side of capacitor 116 is connected to ground potential. The other side of the parallel combination of resistor 102 and inductor 110 is connected to a first side of the parallel combination of resistor 104 and inductor 112 as well as to one side of capacitor 118. The other side of capacitor 118 is connected to ground potential. The other side of the parallel combination of resistor 104 and inductor 112 is connected to a first side of the parallel combination of resistor 106 and inductor 114 and one side of capacitor 120. The other side of capacitor 120 is connected to ground potential. The other side of the parallel combination of resistor 106 and inductor 114 is connected to one side of both capacitor 122 and resistor 108 and the output connection. The other side of capacitor 122 and resistor 108 are connected to ground. Table 1 shows the values of the components depicted in FIG. 3. Tests have shown that the circuit per FIG. 3 reduces the gain of the applied signal by 3 db at a frequency of approximately Alternatively, the filter network 24 tends to smooth the electrical signal per FIG. 2a for generating an output signal of the form shown in FIG. 2c.

Figure 4:
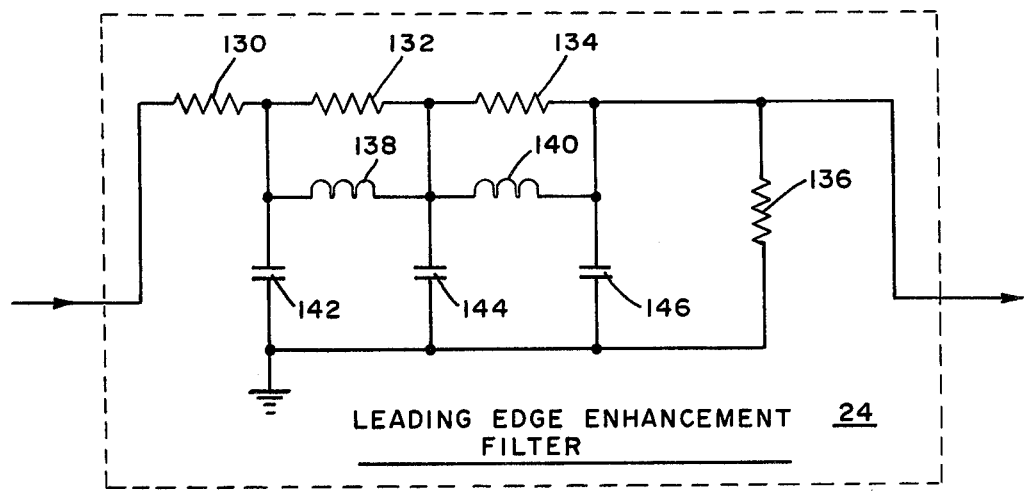
FIG. 4 is a schematic electrical circuit diagram of a preferred embodiment of an alternative filter network for processing video signals to be used in an edge enhanced display.

A preferred embodiment of the filter network 24 is shown in detail in FIG. 4. The input connection is connected to one side of resistor 130. The other side of resistor 130 is connected to one side of capacitor 142 and the parallel combination of resistor 132 and inductor 138. The other side of capacitor 142 is connected to ground potential. The other side of parallel combination of resistor 132 and inductor 138 is connected to one side of capacitor 144 and the parallel combination of resistor 134 and inductor 140. The other side of capacitor 144 is connected to ground potential. The other side of the parallel combination of resistor 134 and inductor 140 is connected to one side of both capacitor 146 and resistor 136 and the output connection. The other side of capacitor 146 and resistor 136 are connected to ground potential. Table 2 shows the values of the components depicted in FIG. 4. Tests have shown that the circuit per FIG. 4 reduces gain by 3 db at a frequency of approximately 250 kilohertz and thereafter the gain curve decreases at a rate of approximately 19 db/octave.

TABLE 2

| Component | Value | Component | Value |
| --- | --- | --- | --- |
| Resistor 130 | 1 kilohm | Inductor 140 | 470 microhenries |
| Resistor 132 | 3.3 kilohm | Capacitor 142 | 470 picofarads |
| Resistor 134 | 3.3 kilohm | Capacitor 144 | 1,000 picofarads |
| Resistor 136 | 1 kilohm | Capacitor 146 | 470 picofarads |
| Inductor 138 | 470 microhenries | | |

Differentiator circuit 26 receives at its input the signal per FIG. 2c and differentiates the signal for providing an output signal in the form of FIG. 2d which latter signal is conducted through switch 28 to amplifier 30. The amplifier 30 preferably exhibits a nonlinear gain function thereby increasing its dynamic range. On the cathode ray tube a point will appear at the position of the screen determined by the output signal from the X- and Y- axis position generator 34, corresponding to the location within the object at which the defect is located at the moment the video signal is applied to the writing electrode. When the entire workpiece is scanned, the image on the screen will appear as a sharply defined leading edge enhanced object from which accurate dimensions may be measured.

It will be apparent that by selectively changing the position of switch 28, either a shades of gray image presentation commensurate with the signals per FIG. 2b or an edge enhanced image presentation commensurate with the signal per FG. 2d is provided on the cathode ray tube. The latter presentation being most useful for simplifying a distance measurement of a portion of the image.

While a preferred embodiment of an ultrasonic imaging apparatus has been described and illustrated, it will be apparent that further variations and modifications may be made without deviating from the broad scope and spirit of the invention which shall be limited solely by the scope of the appended claims.

What is claimed is:

1. An apparatus for improving resolution of an ultrasonic imaging display comprising:

transducer probe means coupled to an object for transmitting an ultrasonic search signal into the object and receiving echo signals arising from the search signal intercepting an acoustic discontinuity and converting said echo signals to electrical signals;

receiver means coupled to said probe means for receiving said electrical signals and providing echo responsive electrical signals;

first filter and differentiator means coupled to said receiver means for receiving said echo responsive electrical signals and producing a first filtered signal commensurate with the amplitudes of said echo responsive electrical signals and differentiating said first filtered signal for providing first video signals having an amplitude commensurate with the amplitude of each of said echo responsive electrical signals;

second filter and differentiator means coupled to said receiver means for receiving said echo responsive electrical signals and producing a second filtered signal commensurate with said echo responsive electrical signals and differentiating said second filtered signal for providing second video signals having an enhanced leading edge of said echo responsive electrical signals;

switch means coupled to said first filter and differentiator means and to said second filter and differentiator means for receiving said first video signals and said second video signals and selectively providing as an output signal either said first video signals or said second video signals, and amplifier means coupled to said switch means for receiving and amplifying said output signal and providing said amplified output signal on a display for displaying an image commensurate with said output signal.

2. An apparatus as set forth in claim 1, said amplifier means being adjustable for having a linear gain characteristic when said output signal is said first video signals and having a logarithmic gain characteristic when said output signal is said second video signals.

* * * * *